United States Patent [19]

Bettarini et al.

[11] Patent Number: 4,540,711
[45] Date of Patent: Sep. 10, 1985

[54] METHOD FOR COMBATTING INFESTATIONS OF INSECTS AND ACARI, AND COMPOSITIONS FOR USE IN SAID METHOD

[75] Inventors: Franco Bettarini, Novara; Pietro Massardo, Milan; Paolo Piccardi, Milan; Angelo Longoni, Milan, all of Italy

[73] Assignee: Montedison S.p.A., Milan, Italy

[21] Appl. No.: 482,261

[22] Filed: Apr. 5, 1983

Related U.S. Application Data

[63] Continuation-in-part of Ser. No. 50,335, Jun. 20, 1979, abandoned, and a continuation-in-part of Ser. No. 198,488, Oct. 20, 1980, Pat. No. 4,356,329, and a continuation-in-part of Ser. No. 355,640, Mar. 8, 1982, abandoned, and a continuation-in-part of Ser. No. 379,177, May 17, 1982, Pat. No. 4,460,606.

[30] Foreign Application Priority Data

Jun. 21, 1978 [IT]  Italy .............................. 24794 A/78
Mar. 5, 1979 [IT]   Italy .............................. 20734 A/78
Jan. 22, 1982 [IT]  Italy .............................. 19237 A/82

[51] Int. Cl.$^3$ .......................................... A01N 31/14
[52] U.S. Cl. ................................................... 514/720
[58] Field of Search ........................................ 424/341

[56] References Cited

U.S. PATENT DOCUMENTS

| | | | |
|---|---|---|---|
| 3,322,813 | 5/1967 | Seki et al. ................ | 568/649 X |
| 3,379,755 | 4/1968 | Schultz ..................... | 568/649 X |
| 3,816,541 | 6/1974 | Mihailovski et al. ....... | 568/649 |
| 4,061,683 | 12/1977 | Karrer ....................... | 568/637 X |
| 4,126,623 | 11/1978 | Piccardi et al. ............ | 260/340.5 R |
| 4,141,921 | 2/1979 | Karrer ....................... | 568/637 |
| 4,153,731 | 5/1979 | Karrer ....................... | 568/637 |

FOREIGN PATENT DOCUMENTS 2528314  1/1976  Fed. Rep. of Germany .

OTHER PUBLICATIONS

Chem. Abst. 93: 141256(v) (1980) Bart et al.
Chem. Abst. 99: 48922(y) (1983)—Banks et al.
Chem. Abst. 99: 171350n (1983) Montedison.

*Primary Examiner*—Douglas W. Robinson

[57] ABSTRACT

There is disclosed a method for fighting infestations of acari or noxious insects including ants, more particularly "fire-ants", by treating the insect, its habitat, or its food with a hydroquinone diether having at least one acetylenic and halogen-substituted chain and selected from 1-[(5-chloro-pent-4-inyl)-oxy]-4-phenoxybenzene of formula

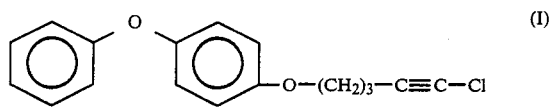
(I)

and 1,4-di-(5-chloro-4-pentinyloxy)-benzene of formula

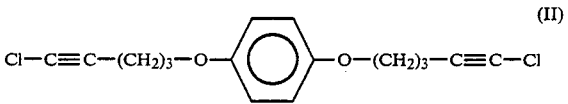
(II)

The disclosure comprises a method for fighting ants using the diether of formula (I) either as such or as an active ingredient of suitable formulations or poisoned baits.

13 Claims, No Drawings

METHOD FOR COMBATTING INFESTATIONS OF INSECTS AND ACARI, AND COMPOSITIONS FOR USE IN SAID METHOD

This application is a continuation-in-part of our earlier filed application Ser. No. 50,335 filed on June 20, 1979 (now abandoned), of our earlier filed application Ser. No. 198,488 filed on Oct. 20, 1980 now U.S. Pat. No. 4,356,329; of our earlier filed application Ser. No. 355,640 filed on Mar. 8, 1982 (now abandoned), and of our earlier filed application Ser. No. 379,177 filed on May 17, 1982, now U.S. Pat. No. 4,460,606 issued on July 17, 1984.

BACKGROUND OF THE INVENTION

U.S. Pat. No. 4,061,683 describes compounds of general formula:

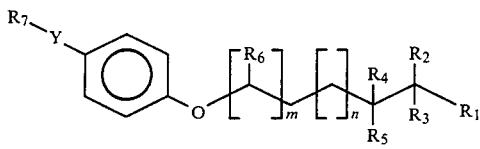

in which $R_1$ is hydrogen, halogen, alkyl, vinyl or ethynyl;
$R_2$ is hydrogen, halogen, methyl or ethyl;
$R_3$ is hydrogen, methyl or alkoxyl;
$R_4$ is hydrogen, halogen or methyl;
$R_5$ is hydrogen or $R_3$ and $R_5$ form a carbon-carbon bond or an oxygen bridge;
$R_6$ is hydrogen or methyl;
$R_7$ is cyclohexyl or a variously substituted phenyl group;
Y is either a methylene or an oxymethylene bridge; and
m and n are either 0 or 1,
as showing insecticide activity against Orthoptera, Isoptera, Hemiptera, Coleoptera, Lepidoptera, Diptera and Acarina.

Among other compounds (col. 17, No. 30 and col. 19, No. 46) the compound

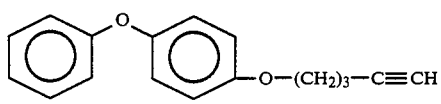

is disclosed.

In U.S. Pat. No. 4,153,731, there are disclosed compounds of the general formula:

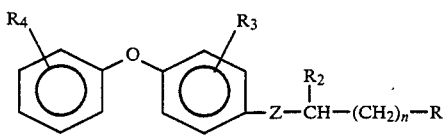

in which
n is 0 or 1;
Z represents oxygen or sulphur;
$R_1$ represents a substituted phenyl group;
$R_2$ represents hydrogen, methyl or ethyl; and
$R_3$ and $R_4$ each represents hydrogen, methyl, ethyl, methoxy, ethoxy, nitro or halogen.

Such compounds are described as able to control a large number of insects, including Acarididae, Tenebrionidae, etc.

U.S. Pat. No. 4,000,312 and U.S. Pat. No. 4,140,794 describe aliphatic compounds having juvenile hormonal activity and a dichloro- or trichloro-substituted end vinyl group bound to a phenyl or substituted phenyl group. Among them, only those having a trichloromethyl terminal group exhibit acaricidal activity.

As to ants, and as is known, the noxious species of ants diffused in all parts of the world are quite numerous and the damages they inflict are found in various fields. For instance, in the agricultural field they may prove harmful both by attacking cultivations or foodstuffs, as well as by rendering the fields intended for cultivations or as pastures unusable.

Other kinds of equally heavy damages will be found in the civil area, because of attacks on wooden buildings and structures, and in the veterinary and medical areas by bites and punctures to cattle as well as humans.

The ant species considered most noxious belong mainly to the following genera: Pheidale, Aphaenogaster, Messar, Oecophylla, Macronischoide, Camponotus, Crematogaster, Iridomyrnex, Atta, Acromyrnex and Solenopsis.

One of the sectors in which there have recently been observed ever-increasing damages and considerable difficulties in controlling such infestations is that of the infestations by ants of the Solenopsis genus in a number of southern states in the United States of America.

It has been calculated that, in the USA, the ants of the Solenopsis genus (called "fire-ants") infest with their ant hills (nests), up to 250 per hectare, and render unusable fields having a total surface of about 80 millions of hectares.

To this type of damages there must be added the losses in cattle killed by the poisonous bite of these insects as well as the serious danger for people living in the neighborhood of infested places or for people frequenting such places.

As a matter of fact, there have been reported quite a number of cases where people had been attacked by such ants and had then died because of a highly sensitivity to the poison injected by their bite.

Earlier, the fight against Solenopsis ants in the USA was carried out using a compound called Mirex, a polycyclic perchlorinated hydrocarbon.

In spite of the good results obtained with that compound, the same was banned when it was discovered that it left residues in human milk and when it was evidenced that it is cancerogenous and teratogenous. Therefore, because of the still growing diffusion of the infestation, it is necessary to find new active products that, at the same time, are harmless for humans and for the environment.

In Belgian Pat. No. 877,164, assigned to Montedison S.p.A., there are described a number of compounds endowed with a juvenile hormonic activity on noxious insects and thus usable in the agrarian and domestic spheres in the fight against insect infestations.

THE PRESENT INVENTION

One object of this invention is to provide an improved and highly effective method for fighting infestations by noxious insects.

Another object is to provide suitable formulations for use in said method for fighting infestations by the noxious insects.

Still another object is to provide a method for fighting infestations by ants, including fire ants.

A further object is to provide suitable formulations, including poisoned baits for fighting the infestations by ants.

These and other objects are achieved by this invention, in accordance with which the infestations are combatted by treating the noxious insect, and/or its habitat and/or its food with at least one hydroquinone diether selected from the diethers of formula (I) or (II), i.e., with an effective dose of 1-[(5-chloro-pent-4-inyl)-oxy]-4-phenoxybenzene or 1,4-di-(5-chloro-4-pentinyloxy)-benzene.

The diether of formula (I) can also be designated as 1-(5-chloro-4-pentinyloxy)-4-phenoxybenzene.

We have found that, among the compounds encompassed by the Belgian Pat. No. 877,164, the compound 1-[(5-chloro-pent-4-inyl)-oxy]-4-phenoxybenzene exhibits an unexpectedly extremely high activity against ants. Moreover, since said diether also exhibits a very low toxicity for warm-blooded animals (at the dose of 3,000 mg/kg no mortality occurred in the acute toxicity tests on rats), and does not appear to be mutagenous in the standard tests that were conducted, it is suitable for use in the fight against ant infestations both in the agricultural field and in environments frequented by humans and by livestock.

In the fight against ants, it is often necessary that the active compound be put into contact also with the larvae of the insects. For this purpose, it proves effective to prepare poisoned baits that nevertheless are desired by the ants, such baits being distributed in the neighborhood of the ant nests so that the worker-ants will introduce the poisoned baits into the nest for nourishing the larvae. The diether of formula I is suitable, also for the preparation of such poisoned baits, and thus, a still further object of this invention is to provide baits containing the compound of formula I diluted in nourishing substances that are appetizing for the ants, and optionally other additives.

In the method of combatting the ants according to this invention, in view of the necessity to kill also the ant-larvae in order to eradicate the infestation, it is preferable to use the product in the form of suitable compositions or poisoned baits.

According to the normal formulating practice, the diether of formula I is used as active ingredient in compositions in the form of a liquid concentrate, a wettable powder or a granular formulate.

In practice, the compositions are then distributed near the ant nests or directly inside the same.

This latter form of application is made possible by the fact that the nests of the ants in general are easily located.

In the above-mentioned compositions, besides the active principle, there may be present the normal inert carriers or additives used in pesticide formulations such as, for instance, liquid or solid vehicles, surfactants, wetting agents, dispersants, antioxidants, etc.

The application of the active ingredient in the form of poisoned baits in general represents the most effective and efficient method of application because, as mentioned above, it is necessary to kill, also, the ant larvae that are deep inside the ant hill. Since the larvae are fed by the worker-ants which gather the nourishment outside the nest, the poisoned baits represent an optimal vehicle for allowing the active compound to reach the larvae in a capillary way.

A necessary condition for an active compound to be used in this type of treatment is that the compound shall possess a delayed action and not be repellant to the ants. Diether I has these characteristics.

The preparation of the poisoned baits is carried out according to conventional formulating techniques. Thus, for instance, the active compound will be incorporated in either liquid or semi-fluid edible substances such as honey, treacle, vegetable oils, proteic lisates, etc., or it may be dissolved in suitable vehicles, including those of alimentary origin, and sprayed on solid edible material such as lyophilized liver, ground cereals, etc.

In general, the bait consists of edible material of proteic, oily or sugary source, besides a quantity of about 0.1%–5% by weight of active substance and, optionally, other suitable additives.

For practical applications of the method for combatting ant infestations according to the invention, the quantity of active substance to be distributed, varies according to several factors. Among these may be listed the type and degree of infestation, the place of infestation, the composition used and the corresponding application means available, and climatic and environmental factors.

In the case of the diether of formula I, and considering the high activity thereof, it is sufficient to use an amount of active substance comprised between 1 and 200 g/ha (preferably between 10 and 20 g/ha) for field applications or about 0.50–50 mg per nest.

In the case of other types of applications, such as the protection of materials and foodstuffs, there will be used the amounts found to be effective for that particular application, also depending on environmental conditions.

The diether of formula I is active, also, against infestations by termites. Considering the known behavioral, social-organizational and habitat analogies, and thus the analogies between the damages caused by ants and termites, the method for fighting ant infestations and the compositions and baits that are objects of the present invention, may be extended, without substantial variations, to the fight against termite infestations.

The hydroquinone diether of formulae I and II, besides exhibiting acaricide activity, exhibit complete activity on *Tribolium confusum*, at 2 p.p.m., *Aedes aegypti* at 0.02 p.p.m.; on *Musca domestica* at 20 p.p.m.; and on Tenebrio at doses of 0.02γ (micrograms, $1/10^6$ g) per insect.

Said hydroquinone diethers show the following $^1$Hnmr spectrum (in $CDCl_3$).

1,4-di-(5-chloro-4-pentinyloxy)-benzene:

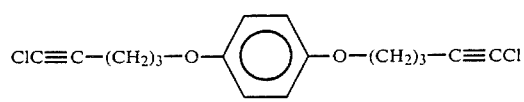

$\delta = 1.7–2.7$ (8H, complex); 3.97 (4H, t); 6.8 (4H, s)

-continued 1-(5-chloro-4-pentinyloxy)-4-phenoxy-benzene:

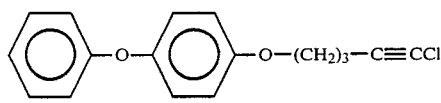

$\delta =$ 1.7–2.6 (4H complex);
3.97 (2H, t);
6.7–7.5 (9H complex)

and may be prepared by reacting the sodium salt of hydroquinone or of phenoxy-phenol with 1,5-dichloro-1-pentine.

Instead of reacting the 1,5-dichloro-1-pentine with the hydroquinone alkali metal salt or with the alkali metal salt of phenoxy-phenol, the hydroquinone alkali metal salt or the alkali metal salt of phenoxy-phenol may be reacted with 1,1,1,5-tetra-chloropentane, followed by dehydrohalogenation of the reaction product at temperatures of 50°–100° C., preferably at 80° C., in dimethylsulphoxide.

The juvenile hormonal activity of the diethers of formulae I and II in comparison with the activity of the compound of formula

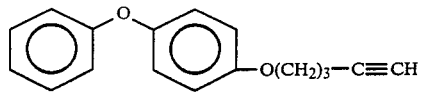

(III)

disclosed in U.S. Pat. No. 4,061,683, has been determined as described in Example 3, infra. The results are summarized in the following Table.

TABLE I

Comparison of the juvenile hormonal activities of compounds I, II, III

| Compound | Tribolium confusum dose 2 ppm | Anagasta kuehniella dose 20 ppm | Aedes aegypti dose 0.02 ppm | Musca domestica dose 20 ppm | Tenebrio molitor dose 0.02 γ/ins. |
|---|---|---|---|---|---|
| I | 100 | 100 | 100 | 100 | 100 |
| II | 100 | 100 | 100 | 100 | 100 |
| III | 0 | 40 | 0 | 0 | 0 |

As appears from Table I, the compounds of the present invention are far more active than compound III, the activity of which latter is recognizable only at 20 ppm on *Tribolium confusum;* at 0.2 ppm on *Aedes aegypti;* at 100 ppm on *Musca domestica* and at 0.2 γ/ins. on *Tenebrio molitor.* It is surprising that the substitution of a terminal H atom by a Cl atom can improve the hormonal juvenile activity 10 times or more.

The following examples illustrate the invention in even more detail, but are not intended to be limiting.

EXAMPLE 1

Preparation of 1,4-di-(5-chloro-4-pentinyloxy)-benzene (JH20)

In 100 ml of DMF (dimethylformamide) were dissolved 5 g of hydroquinone and 4.5 g of NaOH and the solution was stirred for 1 hour at room temperature. 14 grams of 1,5-dichloro-1-pentine were dripped into the solution and the mixture was then heated to 60° C. for 6 hours.

At the end, the reaction mixture was cooled down, poured into water and extracted with ethyl ether. The ether extract was then neutralized with diluted HCl, washed with water, anhydrified with Na$_2$SO$_4$, and finally concentrated. The residue was chromatographed on a silica gel column; by eluting with ether and petroleum ether 95:5, 6 g of 1,4-di(5-chloro-4-pentinyloxy)-benzene were obtained having the following characteristics:

m.p.=62° C.; $^1$Hn.m.r. spectrum (in CDCl$_3$);
$\delta =$ 1.7–2.7 (8H, complex); 3.97 (4H, t); 6.8 (4H, s).

EXAMPLE 2

Preparation of 1-(5-chloro-4-pentinyloxy)-4-phenoxy-benzene (JH286)

Two gms of 4-phenyloxy-phenol were dissolved in 10 ml of dimethylsulphoxide and 1.6 g of milled NaOH were added to the solution. The mixture was then stirred for one hour at room temperature, after which 2.5 g of 1,1,1,5-tetrachloropentane were dripped into the mixture. The mixture was then heated to 60° C. and kept at that temperature for 6 hours.

After 6 hours, the mixture was poured into water, then extracted with ethyl ether. The residue thus obtained, by concentration of the etheric phase, was purified on the chromatographic column as in Example 1. Thereby were obtained 2.1 g of a compound showing the following $^1$Hn.m.r. characteristics (in CDCL$_3$): δ1.7–2.6 (4H, complex): 3.97 (2H, t); 6.7–7.5 (9H, complex).

EXAMPLE 3

Tests of juvenile hormonal activity (a) *Tribolium confusum*

5 g of wheat meal were uniformly treated with an acetone solution of the product. 24 hours after the treatment, the meal or flour was infested with 22 days old larvae. Survey of the results was made about 45 days later when the insects of the witness group had completed emergence from the cocoons.

(b) *Anagasta kuehniella*

5 g of maize meal were uniformly treated with an acetone solution of the product. 24 hours after the treatment, the meal or flour was infested with 21 days old larvae. The survey of the results was made every 3–4 days starting from the first appearance of the adult insects until the end of the emergence from the cocoons in the witness group.

(c) *Aedes aegypti*

3 cc of an acetone solution of the product were added to 297 cc of tap water into which were successively transferred 25 larvae, four days old, supplying them the suitable food. Surveyings of the results were made every 2–3 days until the end of the emergence from the cocoons in the witness group.

(d) *Musca domestica* (larvae)

250 g of artificial nutrient medium were mixed with 5 ml of an acetone solution of the product and then infested with 100 larvae, 2 days old. After 6 days, the pupae in the nutrient medium were collected and kept apart waiting for adults. The results were calculated when all the pupae of the control test (without the substances having juvenile hormonal activity) developed into adults.

(e) *Tenebrio molitor*

0–24 hours aged pupae were treated by topical application on the antepenultimate urosternite with an acetone solution of the products (2 micro liters). A survey of the results was taken after about 9 days when the insects of the witness group completed their emergence from the cocoons.

(f) *Tetranychus urticae*

Eggs—Bean leaves discoids were infested with acari eggs and were then treated by sprinkling on them an aqueous dispersion having a concentration of 1% of the compound under examination. The percent mortality was evaluated as 0 in the untreated leaves discoids.

Adults—Bean leaves discoids were infested with acari adults and successively treated with an aqueous dispersion at 0.1% of the product being tested. The percent mortality was evaluated as 0 for the untreated leaves discoids.

As activity index there was adopted the percentual ratio of dead individuals, misshaped and abnormal individuals with respect to the number of treated individuals, as may be deduced from the following formula:

$$\text{activity} = \frac{(\text{dead} + \text{misshaped} + \text{abnormal individuals})}{\text{treated individuals}} \%$$

The results for hormonal juvenile activity are summarized in Table I; the activity on *Tetranychus urticae* at 1% dose is the following.

TABLE II

Acaricidal activity on *Tetranychus urticae*, adults and eggs, of compounds I, II, III at 1% concentration

| Compound | *Tetranychus urticae* adults | eggs |
|---|---|---|
| I | 83 | 100 |
| II | 18 | 87 |
| III | 18 | 80 |

EXAMPLE 4

This example describes a field-test under natural conditions of ant infestation by fire ants of the Solenopsis genus, carried out in the State of Mississippi (USA) in June 1981, by the U.S. Department of Agriculture, using the compound of formula I supplied by Montedison S.p.A., Milan, Italy. (This relatively large scale field-test had been preceded by a small scale laboratory test in the summer of 1980 by the U.S.D.A. using diether I also supplied by Montedison S.p.A.). On a permanent pasture not open to cattle were selected three plots of about 5 hectares each. In each of these plots were singled out five further sub-plots of 0.1 ha, in which to observe the activity of the ants before and after treatment.

There were then prepared a number of baits consisting of pregel defatted corn grits (70%), once-refined soybean oil (28 or 29%) and diether I (2 or 1%).

The baits were prepared by incorporating diether I in the soybean oil, and this solution was then sprayed on the corn grits maintained under stirring in a mixer. The baits were applied by a distributor for granular formulates, mounted on a tractor.

The bait with 1% of active ingredient (diether I) was applied to a plot at the rate of 1.126 kg/ha (corresponding to a dose of 11.27 g/ha of active ingredient) while the 2% bait was applied to a second plot at the rate of 1.014 kg/ha (corresponding to a dose of 20.28 g/ha of active ingredient). The third plot was left untreated and served as a control.

The evaluation of the effectiveness of the treatment was made by observing the activity of the ants before and after the treatment.

Before the treatment, the area of each plot was examined and the number of ant nests were counted, whereupon to each nest there was assigned an index (nest index) based on the estimated number of worker-ants and on the presence or absence of immature workers (larvae) as indicated in the following Table III.

TABLE III

| Number of worker-ants | Nest Index Absence of immature worker-ants | Presence of immature worker-ants |
|---|---|---|
| <100 | 1 | 6 |
| 100–1,000 | 2 | 7 |
| 1,000–10,000 | 3 | 8 |
| 10,000–50,000 | 4 | 9 |
| >50,000 | 5 | 10 |

Thereafter, a "population index" was determined for each plot by multiplying the number of ant nests, with a certain "nest index", by the index itself and by then summing the totals for the plot.

The comparison between the number of active nests and the population index before and after the treatment provides the means for determining the effectiveness of the treatment.

The following Table IV shows the results obtained 13 weeks after the date of treatment.

TABLE IV

Effectiveness of compound I in a field-test against ants of the Solenopsis genus

| Plot No. | Sub-plot No. | Before treatment Number active nests | Population index | Average index of nests | 13 weeks after treatment[d] Number active nests | Population index | Average index of nests | Percentual variation Active nests | Population Index | Average index of nests |
|---|---|---|---|---|---|---|---|---|---|---|
| 1[a] | 1 | 10 | 95 | 9.50 | 1 | 3 | 3.00 | −88.6 | −96.4 | −68.0 |
|  | 2 | 10 | 90 | 9.00 | 1 | 1 | 1.00 | −88.6 | −98.8 | −88.4 |
|  | 3 | 9 | 82 | 9.11 | 2 | 4 | 2.00 | −74.7 | −94.5 | −77.6 |
|  | 4 | 8 | 69 | 8.63 | 0 | 0 | 0 | −100 | −100 | −100 |
|  | 5 | 9 | 89 | 9.89 | 0 | 0 | 0 | −100 | −100 | −100 |
|  | Total | 46 | 425 | 9.24 | 4 | 8 | 2.0 | −90.1 | −97.9 | −77.9 |
| 2[b] | 6 | 10 | 90 | 9.00 | 2 | 2 | 1.00 | −77.2 | −97.5 | −88.4 |
|  | 7 | 10 | 93 | 9.30 | 1 | 1 | 1.00 | −88.6 | −98.8 | −88.7 |
|  | 8 | 4 | 31 | 7.75 | 1 | 4 | 4.00 | −71.6 | −85.4 | −48.1 |
|  | 9 | 8 | 71 | 8.88 | 2 | 3 | 1.50 | −71.6 | −95.2 | −82.6 |

TABLE IV-continued

Effectiveness of compound I in a field-test against ants of the Solenopsis genus

| Plot No. | Sub-plot No. | Before treatment | | | 13 weeks after treatment[d] | | | Percentual variation | | |
|---|---|---|---|---|---|---|---|---|---|---|
| | | Number active nests | Population index | Average index of nests | Number active nests | Population index | Average index of nests | Active nests | Population Index | Average index of nests |
| | 10 | 10 | 96 | 9.60 | 4 | 7 | 1.75 | −54.5 | −91.7 | −81.3 |
| | Total | 42 | 381 | 9.07 | 10 | 17 | 1.70 | −72.9 | −94.9 | −80.8 |
| 3[c] | 11 | 9 | 83 | 9.22 | 8 | 68 | 8.50 | −11.1 | −18.1 | −7.8 |
| | 12 | 14 | 130 | 9.29 | 8 | 71 | 9.00 | −42.9 | −44.6 | −3.1 |
| | 13 | 17 | 146 | 8.59 | 18 | 170 | 9.44 | +5.9 | +16.4 | +9.9 |
| | 14 | 11 | 88 | 8.00 | 9 | 60 | 6.67 | −18.2 | −31.8 | −16.6 |
| | 15 | 7 | 52 | 7.43 | 8 | 71 | 8.88 | +14.3 | +36.5 | +19.5 |
| | Total | 58 | 499 | 8.60 | 51 | 441 | 8.65 | 0(−12.1)[e] | 0(−11.6)[e] | 0(+0.6)[e] |

Notes to Table IV:
[a]plot treated with baits containing 1% by weight of diether I at a dose of 11.27 g/ha a.i.;
[b]plot treated with baits containing 2% by weight of diether I at a dose of 20.28 g/ha a.i.;
[c]untreated plot used as a control;
[d]data corrected for the variations of the control according to Abbott's formula;
[e]the data between brackets indicate the percentual variation of the control before correction.

EXAMPLE 5

The activity of diether I was determined in a test of a practical character, carried out towards the end of May 1979, in the province of Latina (Italy) on ants belonging to the *Iridomyrnex humilis* species, a species very diffused in Italy and whose harmfulness may often be very high.

There were singled out in one field, and marked for experimental purposes, 6 ant hills each inhabited by several thousands of individuals, said ant hills being located at a suitable distance from each other.

There was then prepared a sugary solution having the following composition:

| | |
|---|---|
| white sugar | 1 kg. |
| water | 1 lt. |
| sodium benzoate | 1.7 g |
| tartaric acid | 1.2 g. |

A suitably shaped vessel containing the sugary solution and that allowed the feeding of the ants but not of bees, was placed near each of three ant hills.

Identical vessels, one for each ant hill, were placed near the other three ant hills, the sugary solution contained in them having been additioned with 2% by weight of diether I previously dissolved in a little acetone.

Six weeks after administering the sugary solution, the ant hills were examined and the level of population present in each of them was assessed.

The ant hills kept as a control and which had been administered the sugary solution not containing diether I, appeared densely populated, while the ant hills which had been fed on a sugary solution additioned with diether I contained only a few tens of individuals and seemed to be undergoing extinction since the absence of larvae was observed.

The procedures and results of the tests are summarized in the following Table V.

TABLE V

| Ant hill No. | Nourishment | Level of population before treatment (approximate No. of individuals) | Level of population 6 weeks after treatment (approximate No. of individuals) |
|---|---|---|---|
| 1 | sugary solution | 2,000–5,000 | 2,000–5,000 |
| 2 | sugary solution | 2,000–5,000 | 2,000–5,000 |
| 3 | sugary solution | 2,000–5,000 | 2,000–5,000 |
| 4 | sug. sol. + 2% comp. I | 2,000–5,000 | ≦150 |
| 5 | sug. sol. + 2% comp. I | 2,000–5,000 | 100 ca. |
| 6 | sug. sol. + 2% comp. I | 2,000–5,000 | <50 |

What is claimed is:

1. A method for combatting infestations of insects or acari, which consists in treating the insect, its habitat, or its food with an insecticidally or acaricidally effective amount of at least 0.02 ppm of a diether selected from the group consisting of 1,4-di-(5-chloro-4-pentinyloxy)-benzene having the formula:

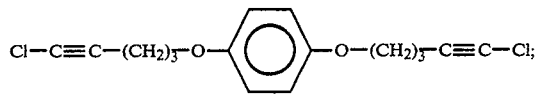

and 1-(5-chloro-4-pentinyloxy)-4-phenoxybenzene having the formula:

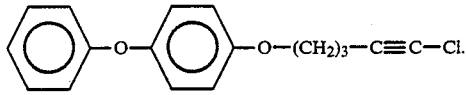

2. The method of claim 1, in which the diether is 1,4-di-(5-chloro-4-pentinyloxy)-benzene.

3. The method of claim 1, in which the diether is 1-(5-chloro-4-pentinyloxy)-4-phenoxybenzene.

4. An insecticidal or acaricidal composition for combatting infestations by insects or acari comprising an insecticidally or acaricidally effective amount of a diether selected from the group consisting of the diether having formula I:

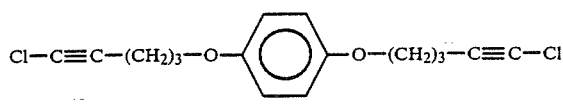

and the diether having formula II

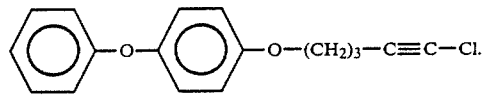

and an acceptable pesticide carrier.

5. A composition according to claim 4, in which the active ingredient is the diether having formula I.

6. A composition according to claim 4, in which the active ingredient is the diether having formula II.

7. A method for combatting infestations by ants by distributing in the infested area an insecticidally effective amount of the diether of formula:

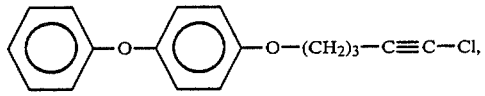

either as such or in the form of a suitable composition or poisoned bait.

8. An insecticidal composition for combatting infestations by ants comprising an insecticidally effective amount of the diether of formula:

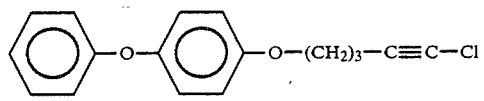

and an acceptable pesticide carrier.

9. A poisoned bait for combatting infestations by ants comprising an insecticidally effective amount of the diether of formula:

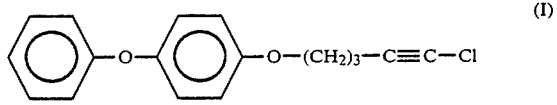

as active ingredient.

10. The poisoned bait according to claim 9, which contains, in addition to the compound of formula I, substances which are appetizing for the ants and, optionally, other additives biologically harmless to forms of life different from ants and termites.

11. The method for combatting ant infestations according to claim 7 in which the ants are of the genus Solenopsis.

12. The method of claim 11 wherein the composition is in the form of a poisoned bait.

13. The method for combatting ant infestations according to claim 7 in which the ants are fire ants.

* * * * *